(12) United States Patent
Chupayak et al.

(10) Patent No.: US 12,409,255 B2
(45) Date of Patent: Sep. 9, 2025

(54) SYNTHETIC POLYISOPRENE LATEX CONDOMS WITH REDUCED NITROSAMINE

(71) Applicant: Thai Nippon Rubber Industry Public Company Limited, Chonburi (TH)

(72) Inventors: Pathompong Chupayak, Chonburi (TH); Theeraphol Piachan, Chonburi (TH); Supparat Piachan, Chonburi (TH); Brian Youichi Kempimook, Chonburi (TH); Punyawat Chupayak, Chonburi (TH); Waranyu Dararattanaroj, Chonburi (TH); Dave Narasimhan, Flemington, NJ (US); Sudarshan Narasimhan, Flemington, NJ (US)

(73) Assignee: Thai Nippon Rubber Industry Public Company Limited, Chonburi (TH)

( * ) Notice: Subject to any disclaimer, the term of this patent is extended or adjusted under 35 U.S.C. 154(b) by 1107 days.

(21) Appl. No.: 17/077,453

(22) Filed: Oct. 22, 2020

(65) Prior Publication Data
US 2022/0125999 A1    Apr. 28, 2022

(51) Int. Cl.
*A61L 31/04*    (2006.01)
*A61F 6/04*    (2006.01)
(Continued)

(52) U.S. Cl.
CPC .............. *A61L 31/049* (2013.01); *A61F 6/04* (2013.01); *C08K 3/06* (2013.01); *C08K 5/42* (2013.01); *A61L 2420/02* (2013.01)

(58) Field of Classification Search
CPC ...... A61L 31/049; A61L 2420/02; A61F 6/04; A61F 6/065; C08K 3/06; C08K 5/39; C08K 5/42; C08K 2003/2296; C08K 2201/014; C08K 5/38; B29K 2007/00; B29K 2105/0064; B29L 2031/7538; C08J 3/26;
(Continued)

(56) References Cited

U.S. PATENT DOCUMENTS

2009/0272384 A1* 11/2009 Lucas ................... C08L 9/00
                                                        427/2.3
2017/0049608 A1*  2/2017 Chiaokun ............... A61F 6/04
(Continued)

*Primary Examiner* — Alireza Nia
*Assistant Examiner* — Gina McCarthy

(57) ABSTRACT

A synthetic polyisoprene latex emulsion has pre-vulcanization composition and post vulcanization composition. The pre-vulcanization composition comprises insoluble amorphous sulfur extracted with zinc dithiocarbamate catalyst at 20° C. to form sulfur chain and transported to interior of synthetic polyisoprene particle forming physical attachment of sulfur to active sites. The degree of pre-vulcanization is verified by expansion of cast and dried film of latex in toluene in 20 minutes by means of a swelling index test. The latex emulsion is vulcanized at 90° C. to 120° C. for 3 to 5 minutes. Post-vulcanization composition with accelerators crosslink between synthetic polyisoprene particles, uniformly curing both in the inter-particle and intra-particle regions to produce high cross link density, uniform distribution of double bonds with zinc segregation at the boundaries of original particles. The condom exhibits high tensile strength, tensile modulus, elongation with excellent tear strength releasing below 10 ppb of nitrosamines.

6 Claims, 4 Drawing Sheets

(51) Int. Cl.
*C08K 3/06* (2006.01)
*C08K 5/42* (2006.01)

(58) Field of Classification Search
CPC ... C08J 5/02; C08J 5/0025; C08L 9/10; C08L 9/00; C09D 171/02; C08C 3/00; C08F 36/08
See application file for complete search history.

(56) References Cited

U.S. PATENT DOCUMENTS

| | | | |
|---|---|---|---|
| 2019/0031788 A1* | 1/2019 | Kodemura | C08C 3/00 |
| 2019/0177496 A1* | 6/2019 | Chen | C08K 5/38 |
| 2020/0239607 A1* | 7/2020 | Nguyen | C08F 36/08 |
| 2021/0189103 A1* | 6/2021 | Toliver | C09D 171/02 |

* cited by examiner

SYNTHETIC POLYISOPRENE LATEX CONDOMS WITH REDUCED NITROSAMINE

FIELD OF THE INVENTION

The invention relates to producing highly stretchable synthetic polyisoprene latex condoms with reduced amount of nitrosamine and method.

FIELD OF THE INVENTION

The present invention relates to manufacture of dip formed synthetic polyisoprene condoms including formers of condoms being dipped in a pre-vulcanized synthetic polyisoprene latex emulsion at reduced temperature thereby reducing or eliminating the formation of cancer causing nitrosamine. See https://www.who.int/ipcs/publications/cicad/en/cicad38.pdf. Accordingly, the latex condom producing environment is free from nitrosamine typically below 8.6 mg/kg of rubber nipples Sen et al 1984, Sen N P, Seaman S, Clarkson S, Garrod F, Lalonde P (1984) Volatile N-nitrosamines in baby bottle rubber nipples and pacifiers. Analysis, occurrence and migration. IARC scientific publications, 57:51-57 and there is minimal or non-detectable level of nitrosamine contamination to the skin contacting regions of the user.

DESCRIPTION OF THE PRIOR ART

In dip molding processes, the majority of work with natural polyisoprene has been focused on the development of polyisoprene condoms and gloves, using a dip process. In this type of process, a glove-shaped mold is first dipped into a coagulant solution that is known to destabilize the latex formulation. This coagulant layer is then dried, before the mold is dipped into a bath of a compounded latex formulation. The coagulated wet latex gel is typically leached in water to remove residual surfactant present in the compounded latex formulation before being dried at a relatively high temperature to complete the cross-linking of the rubber film. Condom formers are dipped without a coagulant.

The use of vulcanizing or sulfur cross-linking agents in the manufacture of rubber articles is well known. The effectiveness of sulfur crosslinking agent is improved by conventional accelerators including dithiocarbamate, thiazoles, guanidines, thioureas, amines, disulfides, thiurams, xanthates and sulfonamides. The use of vulcanizing agents in the manufacture of polyisoprene rubber is disclosed in D'Sidocky et al., U.S. Pat. No. 5,744,552, and Rauchfuss et al., U.S. Pat. No. 6,114,469.

Attempts have been made to use multiple accelerators in vulcanizing polyisoprene latex.

U.S. Pat. No. 4,695,609 to Stevenson discloses vulcanizable rubber compositions containing less than 0.4 parts by weight of nitrosatable materials per 100 parts by weight rubber, of xanthogen polysulfide and xanthate compounds. This rubber composition contains a dihydrocarbyl xanthogen polysulphide and a xanthate selected from metal hydrocarbylxanthates and dihydrocarbylxanthates. The aqueous latex emulsion 9E contains sulfur, zinc oxide and zinc diethyldithiocarbamate, and is stable for only four days and has a low tensile strength at fracture, making this unsuitable for a manufacturing process.

U.S. Pat. No. 5,254,635 to Stevenson discloses a rubber composition containing dibenzylthiuram sulfide. A dibenzylthiuram sulfide, such as tetrabenzylthiuram disulphide, is combined with a dihydrocarbyl xanthogen polysulphide and/or a xanthate to provide a composition, which cross-links natural rubber at 120-180° C. without providing harmful nitrosatables. This natural latex composition, however, is sulfur-free and does not cross-link intra particle regions of a synthetic cis-1,4-polyisoprene having low levels of stereoregularity. Therefore, the use of these cross-linking agents for natural polyisoprene latex will result in a non-uniform article with inferior properties.

U.S. Pat. Nos. 6,653,380 and 7,048,977 to Dzikowicz disclose Latex film compound with improved tear resistance. The method enhances the tear resistance, tensile strength, and the aging properties of a latex product by adding an antioxidant synergist with an antioxidant to a latex compound. The latex compound comprises a polymer, a stabilizing system, a film surface conditioner and a curing system that comprises an activator, crosslinker and accelerator. Antioxidant synergists include 2-mercaptobenzimidazole (MBI), 2-mercaptotoluimidazole (MTI), zinc 2-mercaptobenzimidazole (ZMBI) and zinc 2-mercaptotoluimidazole (ZMTI). The latex products formed may be gloves but can also include threads, balloons and other latex-related products. The latex used with the addition of anti-oxidants does not pre-vulcanize the polyisoprene latex.

U.S. Pat. No. 6,828,387 to Wang et al. discloses polyisoprene articles and a process for making the same. This process produces polyisoprene articles exhibiting tensile strength properties similar to those of solvent-based processes using natural rubber latex. The process combines a synthetic latex with sulfur, zinc oxide and an accelerator composition comprising a dithiocarbamate, a thiazole, and a guanidine compound, all three of which need to be present, at the pre-cure stage. In a preferred embodiment, the accelerator composition comprises zinc diethyldithiocarbamate (ZDEC), zinc 2-mercaptobenzothiazole (ZMBT), and diphenyl guanidine (DPG), in conjunction with a stabilizer, which is primarily milk protein salt, such as sodium caseinate. Polyisoprene latex (typically 60% solids) and the stabilizer (e.g., sodium caseinate) are combined at ambient temperature (about 20-25° C.). After mixing for a period of time, the mixture is then diluted to 40% solids in water. Wingstay L is then added, and the mixture is stirred for approximately 15 min. At this point, the pH can be adjusted to a range of about 8.5 to 9.0. Zinc oxide is added, followed by the sulfur and accelerator compounds. The elastomeric polyisoprene product made by the process is a surgeon's glove dipped over a coagulant-coated former. The aqueous latex emulsion is only minimally stable with a maximum stability of eight days. The tensile strength of the surgical glove product obtained is approximately only 3,000 psi or 20.6 MPa. The accelerators are added to the latex emulsion, but maintained at a low temperature for up to eight days. The stability of this aqueous latex composition is better than that of Stevenson (U.S. Pat. No. 4,695,609), but is still inadequate for a manufacturing process. The glove formers are dipped in a coagulant solution containing calcium nitrate that is unsuited for coagulant-free dipping of condoms.

U.S. Pat. No. 7,041,746 to Dzikowicz discloses accelerator system for synthetic polyisoprene latex. This accelerator system comprises dithiocarbamate and thiourea and can produce synthetic polyisoprene films having a tensile strength of about 3,000 psi to about 5,000 psi at low curing temperatures. These accelerators are not indicated to pre-vulcanize the polyisoprene particles and the latex article produced has a very low modulus of 1.5 MPa at 300% elongation.

U.S. patent application Ser. No. 2002/0173563A1 describes a process for making dipped articles from latex involving the use of an accelerator system comprising zinc diethyldithiocarbamate ("ZDEC"), zinc 2-mercaptobenzo-thiazole ("ZMBT"), and diphenyl guanidine ("DPG"). ZDEC with the ZMBT is a popular accelerator system for natural rubber latex. Only the addition of DPG allows this accelerator system to achieve cured films with tensile strengths in excess of 3,000 psi (20 MPa).

UK patent application GB 2,436,566 to Attrill et al. discloses minimizing pre-vulcanization of polyisoprene latex. This process for making a polyisoprene latex comprises compounding a synthetic polyisoprene latex with compounding ingredients and maturing the latex at a low temperature so as to minimize pre-vulcanization. Dipping of condoms is also conducted at low temperatures typically 15° C. to less than 20° C. The absence of pre-vulcanization is verified by assuring the strength of a ring made has a prevulcanisate relaxed modulus with a value less than 0.1 MPa indicative of the absence of pre-vulcanization. The latex emulsion may contain accelerator such as dithiocarbamate. The '566 patent application teaches away from pre-vulcanization prior to dipping of latex articles.

Nitrosamines are produced when rubber latex is vulcanized at high temperatures and are produced by the reaction of nitrite with secondary amine.

U.S. Pat. No. 6,495,065 to Lou, et al. discloses Nitrosamine-inhibiting compositions for shortstopping of free radical emulsion polymerizations. This method of shortstopping free radical emulsion polymerizations inhibits the formation of nitrosamines. The composition comprises nitrosamine inhibitors in combination with conventional alkylhydroxylamine shortstoppers. Such nitrosamine inhibitors are based on primary amines, amine-containing polymers, pyrroles, hydroquinones, certain phenols, ascorbic acid, and other well-known nitrosation inhibitors; they may be used individually or as a blend. The compositions are targeted for applications in the emulsion processes for producing rubber latexes and the preparation of rubber products.

World patent 97/32927 to Gibbs et al discloses inhibiting nitrosamine formation in rubber. This process for reducing or inhibiting nitrosamine formation in vulcanizable rubber comprises incorporation of alkaline earth metal carboxylate or phenate. These compounds have a melting point below 130° C.

The publication at IARC Sci Publ 1982; (41): 231-43 deals with nitrosamine and rubber. Occupational exposure to N-nitrosamines in the rubber industry was first reported by Fajen et al. (1979). In order to study the origin and formation of nitrosamines in this industry, chemicals and industrial products, as well as the air in various working areas, were analyzed (Spiegelhalder et al., 1980). All chemicals used for rubber compounding contain nitrosamines if they are derivatives of secondary amines; e.g., tetramethylthiurame, zinc-diethyldithiocarbamate or N-oxydiethylene benzothiaz-olylsulfenamide. All rubber products containing these dialkyl amine derivatives exhibited considerable levels of the corresponding nitrosamines. Accordingly, variable concentrations of airborne nitrosamines could be detected at places where rubber products are manufactured or stored. The nitrosamines found correspond to the compounded chemicals. The original nitrosamine level in rubber chemicals is not high enough to explain the amounts found in rubber products and in air, so that additional nitrosation must occur. The responsible nitrosating agents are described. Preliminary results show that, in most cases, the elimination of nitrosating agents or the use of different rubber chemicals can drastically reduce nitrosamine levels in rubber products and in working areas.

There is a need, therefore, for a high elongation stretchable latex articles including synthetic polyisoprene condoms made by dipping a former in a stable polyisoprene latex emulsion composition that does not agglomerate or flock and provides usable emulsion lifetimes. The production of these condoms should not release nitrosamine in the production environment and the level of nitrosamines in the condoms should be minimal, thereby preventing the release of cancer causing compounds to the user. The composition must achieve intra-particle and inter-particle crosslinking in the final product. Such a composition would enable the dip-forming of articles with or without use of a coagulant, such that articles have thinner, continuous, and defect-free layers with enhanced strength and improved stretchability. Such articles would not deteriorate and would maintain their physical integrity over time. It is an object of the present invention to provide such a composition, as well as a method of preparing and using such a composition to dip-form synthetic polyisoprene articles including condoms and gloves, and the articles so produced. These and other objects and advantages, as well as additional inventive features, will become apparent from the detailed description provided herein.

SUMMARY OF THE INVENTION

The invention relates to producing highly stretchable synthetic polyisoprene latex condoms with reduced amount of nitrosamine and method.

The process for producing high quality condoms from synthetic polyisoprene involves the use of multiple accelerators that activate effectively at different temperatures, creating a bond between polyisoprene molecule and sulfur that is provided. All the sulfur provided is exhausted creating physical bonds with the polyisoprene molecule without over curing the bonds at each temperature forming a chemical bond between sulfur and polyisoprene.

The quantity of available sulfur is limited and as the mixing temperature is increased 20 to 40° C., different accelerators provided in the latex bath activate sulfur, pre-vulcanizing the polyisoprene latex until all the bond sites are exhausted. This pre-vulcanization places sulfur atoms physically at appropriate locations within the polyisoprene polymer molecule and are fully reacted forming chemical bonds during the vulcanization cycle.

Since the temperature of pre-vulcanization is low and vulcanization is carried out at a temperature range of 90° C. to 120° C. no nitrosamines are formed. The material composition of the condom produced is tested for nitrosamines.

The latex condom has controlled pre-vulcanized particles of synthetic polyisoprene latex that are pre-vulcanized by a plurality of accelerators that individually activate as the temperature of the latex is increased from 20° C. to 40° C. A thin latex condom is dip formed using the pre-vulcanized aqueous latex emulsion and vulcanized for a short time at a reduced temperature of only 90° C. to 120° C. The cured latex condom is a highly stretchable synthetic rubber body that has an elongation of about 900% and is extremely tear resistant.

Manufacture of latex articles that are vulcanized at a high temperature results in the production of cancer causing nitrosamine, which is generally present in the latex manufacturing location and has the potential to harm workers. In addition the latex articles thus produced also carry the cancer producing nitrosamine, which is transferable to the skin contacting locations of the user. There is a need therefore for a synthetic polyisoprene article producing process that minimizes the production of nitrosamine both in the work environment and the latex articles thus produced.

The product thus produced has several distinguishing features that have imprints of this pre-vulcanization methodology. Since the synthetic polyisoprene thin film of latex is cured with improved crosslink density, the molecular weight between crosslinks exhibits a lower value. Since zinc complex of dithiocarbamate catalytically breaks the Ss ring of sulfur and as a catalyst, it is available for subsequent use and does not readily penetrate the synthetic polyisoprene due to its large molecular size. The molecular size of zinc dibutyldithiocarbamate is a larger than that of zinc diethyldithiocarbamate which has a molecular size greater than that of zinc dimethyldithiocarbamate. Zinc dibenzyldithiocarbamate and zinc diphenyldithiocarbamate are even larger molecules and will resist permeation into the natural polyisoprene latex particles. Thus the preferred zinc complex of dithiocarbamate for pre-vulcanization of synthetic latex particles in the latex emulsion is zinc dibutyldithiocarbamate (ZDBC) or zinc diethydithiocarbamate (ZDEC). There is an accumulation of zinc containing compounds surrounding each of the original synthetic polyisoprene particles, and this microstructural feature can be readily observed by microprobe elemental analysis using an electron microscope. The synthetic polyisoprene films produced typically have acceptable tensile strength, high tensile modulus and elongation at fracture with the fracture front passing through both the inter particle and intra particle regions indicating that the intra particle regions and inter particle regions are substantially of equal strength within the natural latex films produced.

The method for producing synthetic polyisoprene condom comprises use of a synthetic latex emulsion that is a pre-vulcanized composition. Preferably, the synthetic polyisoprene particles are cis-1,4-polyisoprene, have a diameter in the range of about 0.2 to 2 micrometers, and are maintained in an aqueous medium of the latex emulsion. The pre-vulcanized composition has sulfur with sulfur extracted from amorphous sulfur source by catalyst of ZDBC, typically of the $S_8$ ring structure broken by zinc dithiocarbamate accelerator disrupting the $S_8$ sulfur ring structure. A combination of surfactants including Hostapur SAS is used to deliver the broken sulfur molecule to the latex. The pre-vulcanization of the synthetic latex particles in the synthetic latex emulsion occurs over a period of 12 hours during the mixing process and an additional 12-24 hours in the maturation tank depending on the temperature of the latex emulsion which is generally in the range of 20° C. to 40° C. The degree of pre-vulcanization of the synthetic latex particles is monitored by a change in diameter of dried film on toluene for 20 minutes using a swelling index test.

A typical synthetic polyisoprene latex emulsion composition is provided in terms of 100 parts by weight of dry rubber (phr). Sulfur crosslinking agent is in the range of 0.6 to 1.8 wt %; ZDEC and/or ZDBC accelerator is in the range of 0.3 to 1.0 wt %; SDBC accelerator is in the range of 0.05 to 0.5 wt %; DXP accelerator is in the range of 0.2 to 0.8 wt %. Reactive zinc oxide activator is in the range of 0 to 0.5 wt %; Hostapur SAS is in the range of 0.1 to 0.5 wt %; SDBS surfactant is in the range of 0.1-0.35 wt %; Polyoxyethylene cetyl/stearyl ether surfactant may be in the range of 0.1 to 0.5 wt %; Winsgtay L or butylated reaction product of p-cresol & dicyclopentadiene anti-oxidant preservative is in the range of 0.3 to 1 wt %; Ammonium hydroxide is in the range of 0 to 0.36 wt %. As indicated earlier, the pre-vulcanization composition of the synthetic polyisoprene latex composition includes sulfur extracted from amorphous sulfur by ZDEC and/or ZDBC accelerator, Hostapur SAS and/or potassium caprylate surfactant and SDBS surfactant and polyoxyethylene cetyl/stearyl ether surfactant. The pre-vulcanization composition provides the availability of sulfur to synthetic polyisoprene latex particles in the aqueous synthetic polyisoprene emulsion and subsequently crosslinks the entire particle of synthetic polyisoprene during vulcanization cure cycle. The post-vulcanization composition provides the ability to crosslink regions between the particles of synthetic polyisoprene thereby assuring a high quality substantially uniformly cured synthetic polyisoprene product.

While this process works successfully to make synthetic polyisoprene condoms, it may used to also produce probe covers. The probe is like a condom but does not have a reservoir at the tip of the condom. Because it has no nitrosamine, the probe does not transfer any cancer causing ingredients to the user.

DETAILED DESCRIPTION OF THE INVENTION

Figure 1:
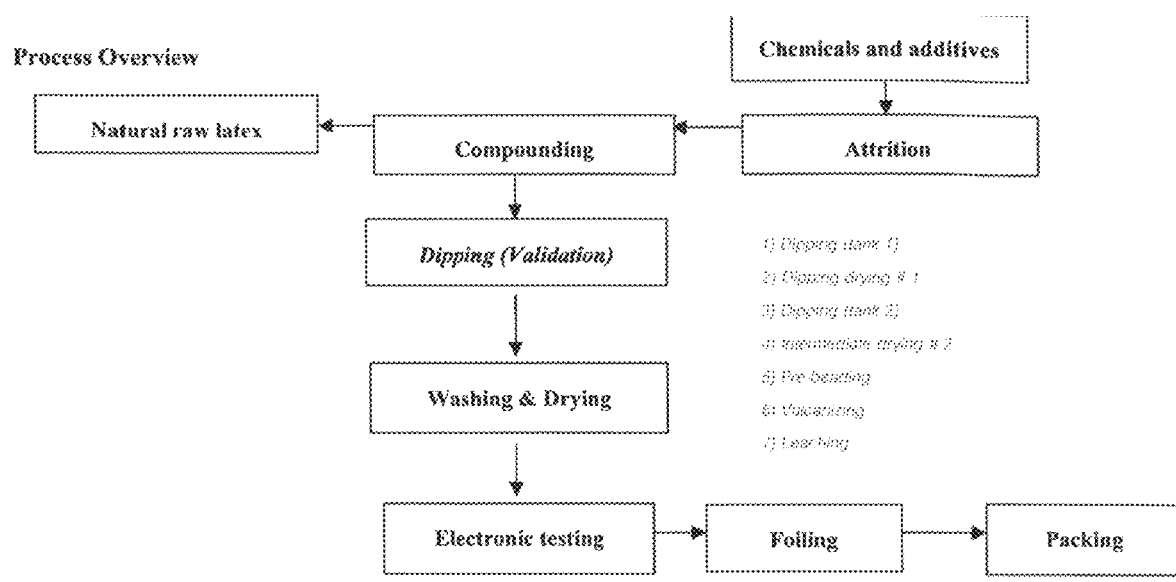
FIG. 1 illustrates the steps used in the current process for manufacturing condoms from synthetic polyisoprene.
Figure 2:
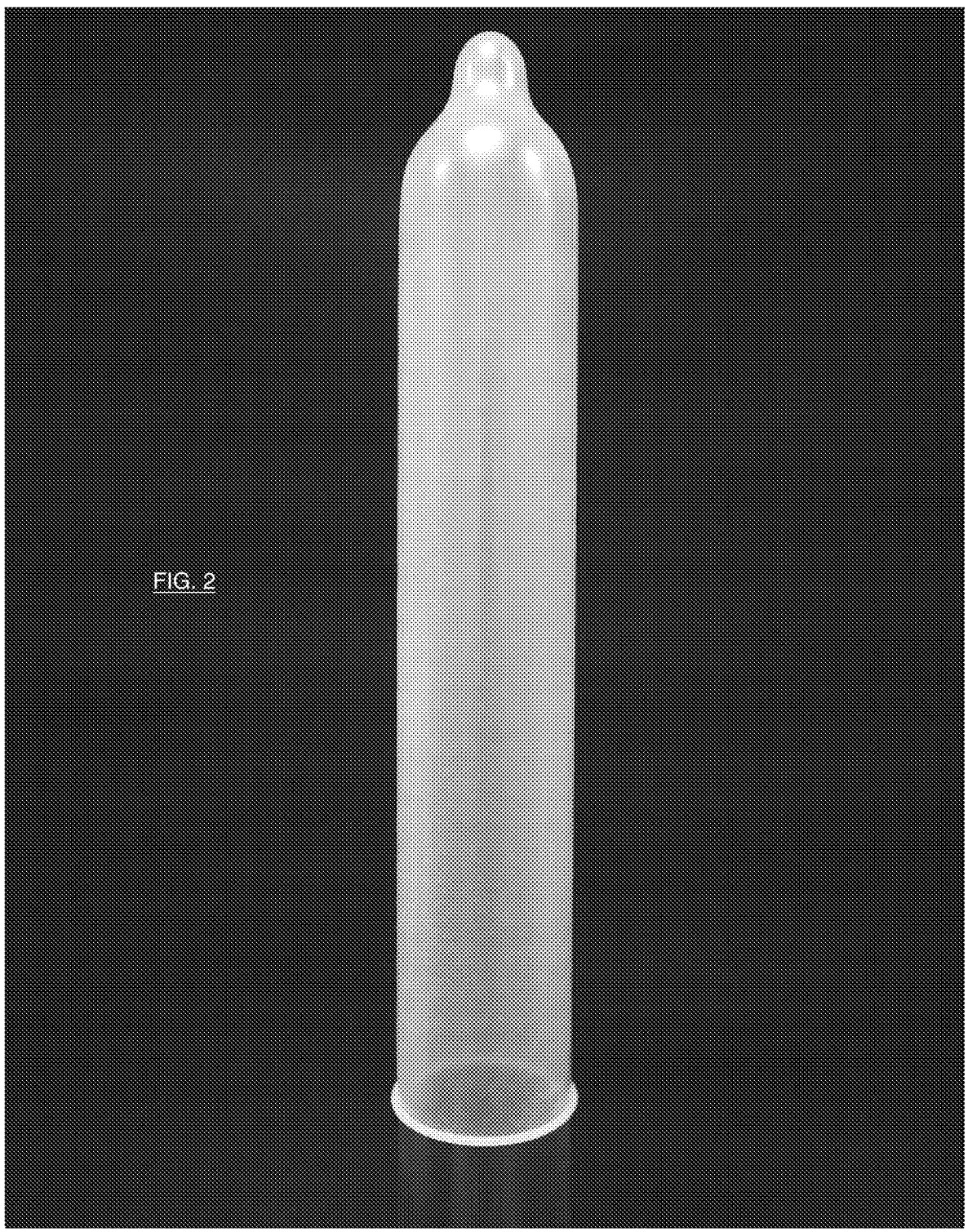
FIG. 2 shows the condom in an unrolled form.
Figure 3:
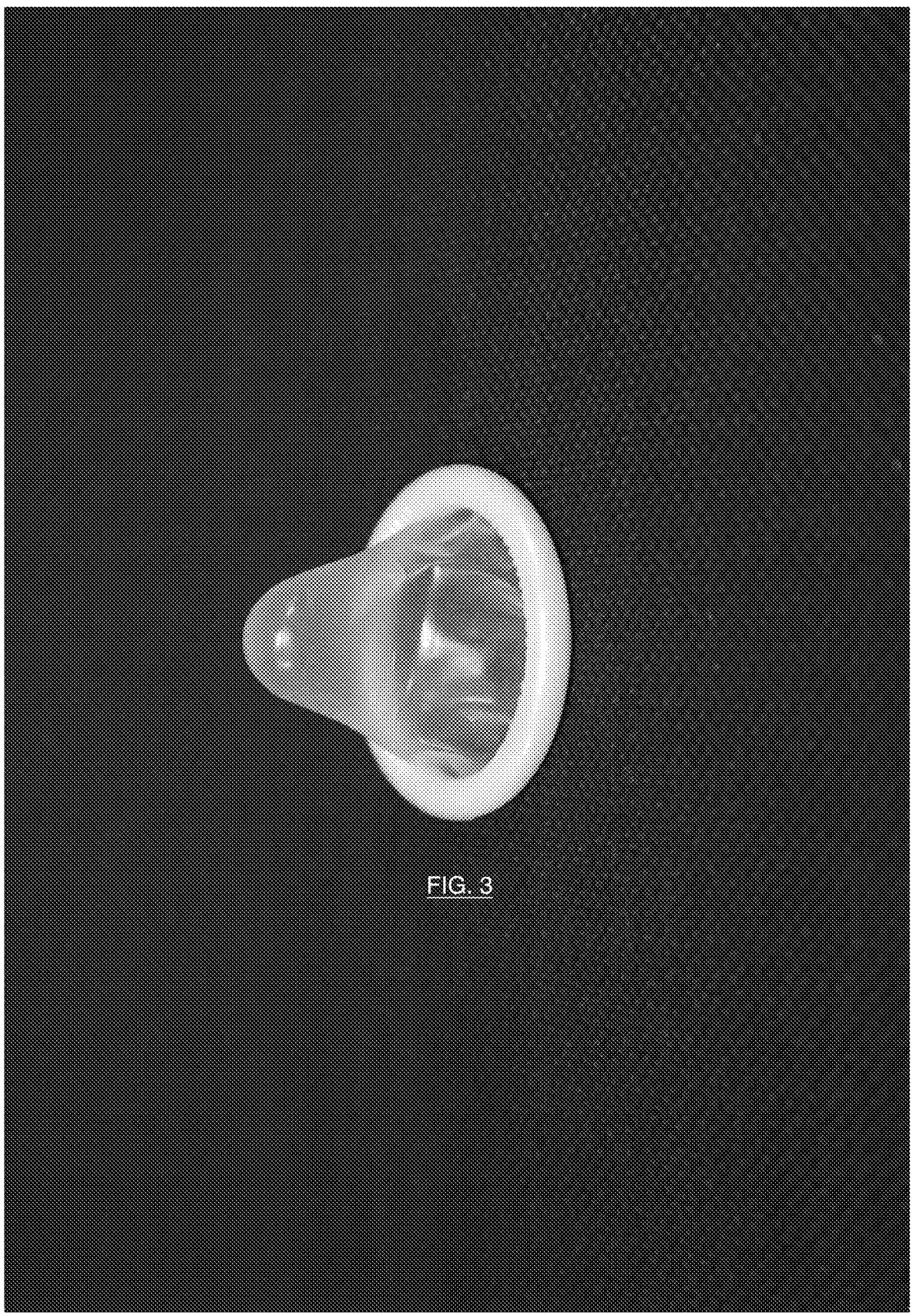
FIG. 3 and 4 show the condom from different angles in a rolled up form.
Figure 4:
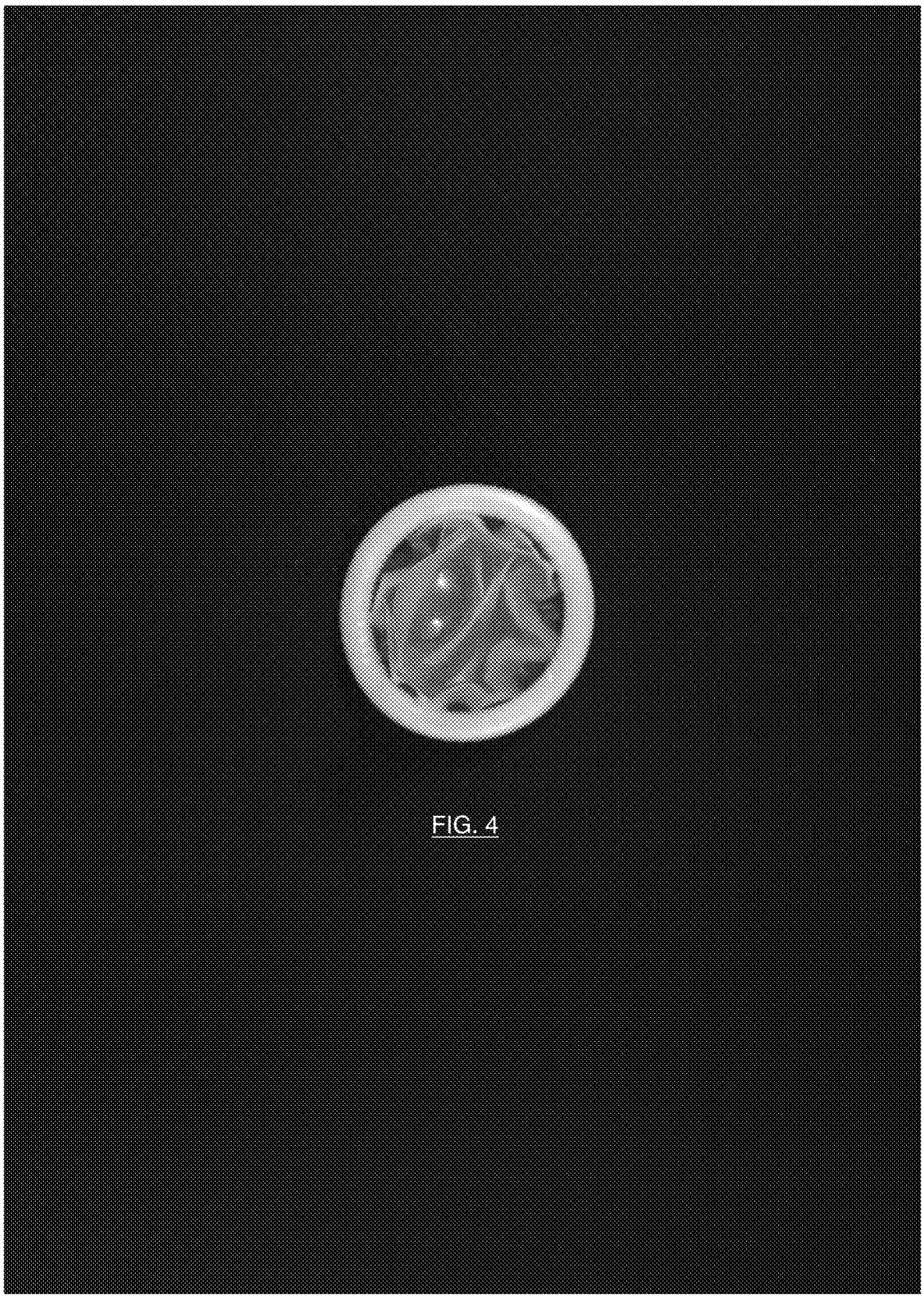

A condom is made from synthetic polyisoprene rubber having a combination of accelerators that cure at different progressively increasing temperatures ensuring the compete cure of the polyisoprene condom without over curing any of the accelerator cured polyisoprene due to exhaustion of sulfur vulcanizating agent at each location.

Since the vulcanization temperature is low, the formation of nitrosamines is limited. Nitrosamines are produced by the reaction of nitrite with secondary amines and is highly temperature dependent. N-Nitrosodiethylamine (NDEA) is the most potent carcinogen among the nitrosamines.

The process for producing synthetic polyisoprene condoms is as follows: First, a 15% Hostapur SAS anionic surfactant is prepared by mixing in deionized water at 50° C. Next, 10% potassium oleate solution is prepared.

The chemicals used in the process and their function is detailed below.
Sulfur: vulcanizing agent
Active zinc oxide: activator
Butylated reaction product of p creosol and dicyclopentadiene: antioxidant
Zinc diethyldithiocarbamate (ZDEC): accelerator
Zinc dibenzyldithiocarbamate (ZBEC): accelerator
Zinc dibutyldithiocarbamate (ZDBC): accelerator
Potassium hydroxide: stabilizing agent
The procedure of adding of these chemicals is detailed below:
Transfer 600 Kg of polyisoprene latex into mixing tank and agitate for 15 min
Agitate colloidal sulfur 7.8 Kg for 15 min
Add 15% Hostapur SAS surfactant solution 6.48 Kg
Add 10% Potassium oleate solution 3.78 Kg
Add 15% Eumulgin solution 7.68 Kg
Add zinc oxide activator 0.36 Kg for 15 min
Add antioxidant 3.89 Kg for 15 min Add ZDEC 3.89 Kg for 15 min
Add ZBEC 0.79 Kg for 15 min
Add 15% Hostapur SAS solution 1.2 Kg
Add ZDBC 0.72 Kg for 15 min
Add 1.23% potassium hydroxide 28.8 Kg water+0.38 Kg KOH
Agitate for 12 hours During this period the catalytic action of ZDBC reacts with colloidal sulfur breaking down sulfur S8 rings and creating linear chains of sulfur that are carried into the synthetic polyisoprene tangled chains by the Hostapur SAS surfactant. Sulfur atoms of the sulfur chains attach to the chains of synthetic polyisoprene within the polyisoprene particle creating pre-vulcanization.

Since all accelerators are mixed together and added to synthetic polyisoprene, they all react based on the process temperature conditions. At low temperature, for example, 20 C, ZDBC catalytically reacts with colloidal sulfur breaking the S8 rings, forming a linear chain of sulfur, which enters the tangled synthetic polyisoprene particle with the help of the surfactant present. ZDEC also enables the attachment of sulfur from the linear sulfur chain to active sites in the polyisoprene molecule creating pre-vulcanization. As the temperature of the polyisoprene bath is raised to around 20° C.-40° C., all the accelerators react with the external surfaces of the polyisoprene particles attaching sulfur atoms to synthetic polyisoprene particle outer surface providing pre-vulcanization.

Prior to dipping of condoms the degree of pre-vulcanization is determined by the swelling index of latex in toluene. A 20 mm diameter dried disk of latex rubber film is made and is immersed in toluene for 20 minutes to expand the disk, and is measured. Un-vulcanized rubber expands to 160% of the original size. Lightly vulcanized rubber swells from 100% to 160%. Moderately vulcanized rubber swells to 80% to 100%. Fully vulcanized rubber swells to 75%. In our process, the latex is considered to be mature is ready for dipping condoms when the swelling index is 130%.

Dip tank 1 latex temperature <40° C.
Dip tank 2 latex temperature <40° C.
Latex dip temperature from 20° C. to 30° C.
Vulcanizing oven 90° C. to 120° C.

The present invention is predicated on the discovery of amorphous sulfur such as S8 rings of sulfur that is catalyzed by a zinc complex of dithiocarbamate in combination with Hostapur SAS surfactant creating pre-vulcanized synthetic polyisoprene particles in a latex composition. This latex composition enables the production of condom latex film articles by dipping coagulant free formers into the latex composition. The surfactant package inhibits synthetic polyisoprene particle agglomeration and flocculation. The latex dipped film has synthetic polyisoprene particles that become crosslinked and regions between the particles are cross-linked during the vulcanization cure forming both intra-crosslinked and inter-crosslinked bonds. The articles that result comprise a high quality and uniform latex film.

The latex-stabilizing composition is one that keeps the particles of synthetic polyisoprene separated from each other in the aqueous medium. Since the polyisoprene particles do not touch each other, they are unable to agglomerate and flock. This is important because, once the particles begin to agglomerate, the particles may never be separated due to Van der Waals forces. Preferably, the latex-stabilizing composition comprises a Hostapur SAS surfactant package. An anionic surfactant is preferred, especially one that can be stably maintained for a period of well over one month and up to two months or more. An example of such a surfactant is sodium dodecyl benzene sulphonate (SDBS). Other examples include, but are not limited to, other alkyl aryl sulphonates, alkyl sulphonates (e.g., C14 olefin sulphonate, which is sold under the trade name Calsoft AOS-40 (Pilot Chem. Co., Red Bank, NJ)), olefin sulphonates, and alcohol sulphates (e.g., sodium lauryl sulphate). SDBS or another alkyl aryl sulphonate is preferably present in an amount of about 0.1-0.35 wt %, based on the dry weight of the polyisoprene. SDBS or another alkyl aryl sulphonate can be combined with one or more other surfactants, such as potassium caprylate, polyoxyethylene cetyl/stearyl ether, and the like. For example, SDBS or another alkyl aryl sulphonate can be combined with potassium caprylate, alone or in further combination with polyoxyethylene cetyl/stearyl ether. When SDBS or another alkyl aryl sulphonate is used in combination with one or more other surfactants, preferably each surfactant is present in an amount of about 0.05-1.2 wt %, based on the dry weight of the synthetic polyisoprene, and the total amount of the surfactant package is about 0.4-1.2 wt %, based on the dry weight of the polyisoprene. When SDBS or another alkyl aryl sulphonate is used in combination with potassium caprylate and polyoxyethylene cetyl-stearyl ether, preferably the polyoxyethylene cetyl-stearyl ether is present in an amount of about 0.1-0.5 wt %, based on the dry weight of the polyisoprene.

In view of the above, the present invention provides a surfactant-stabilized, pre-vulcanized, synthetic polyisoprene latex composition having an expansion of about 130% when a cast and dried film of synthetic polyisoprene is immersed in toluene for 20 minutes. The consistency of the coagulum indicates the degree of pre-vulcanization of the latex. As the latex becomes more pre-vulcanized, the coagulum loses more of its tackiness and becomes more crumbly. An expansion of about 130% indicates that the synthetic polyisoprene is ready for the dipping of condoms. The pre-vulcanized synthetic polyisoprene may be stored indefinitely at 20° C. to 30° C.

The pre-vulcanization composition includes potassium caprylate and SDBS or another alkyl aryl sulphonate surfactant with zinc dithiocarbamate and amorphous sulfur that is extracted by ZDBC. The latex emulsion with surfactants wets the synthetic polyisoprene particles, the catalytic action of zinc dithiocarbamate breaks the ring of amorphous S& molecule forming a linear chain of sulfur that pre-vulcanizes particles of synthetic polyisoprene. The post-vulcanization composition has sulfur and other accelerators that cause inter-particle cross-linking during the vulcanization cure. Such cross-linking results in a more homogeneous latex film having greater strength and elongation properties and cross-link density.

Preferably, the pre-vulcanizing composition comprises (i) a cross-linking package comprising zinc diethyldithiacarbamate or zinc dibutyldithiocarbamate accelerator and sulfur and (ii) a wetting agent. During pre-vulcanization, sulfur with its ring structure is broken by the catalytic action of the zinc dithiocarbamate accelerator that penetrates the polyisoprene particles and initially interacts with the isoprene double bonds therein. The catalytic reactivity of zinc dithiocarbamate is detailed in the publication entitled "The Mechanism of Zinc (II)-Dithiocarbamate-Accelerated Vulcanization Uncovered; Theoretical and Experimental Evidence" by Nieuwenhuizen, et al. is published in J. Am. Chem. Soc., 121 (1), 163-168, 1999. A second publication entitled "Zinc accelerator complexes. Versatile homogeneous catalysts in sulfur vulcanization" by Nieuwenhuizen published in Applied Catalysis A: General 207 (2001) 55-68. These two publications discuss the mechanism of catalytic action of zinc dithiocarbamates specifically zinc dimethyldithiocarbamate with sulfur. The sulfur gets captured within four atoms of zinc in the accelerator molecule and moves in and out as a catalytic activity. The book published by Garry R. Hamed, professor at University of Akron, the chapter 2 of which is available at web address files.hanser.de/hanser/docs/20040401_244515439-6683_3-446-21403-8.pdf clearly indicates in Chapter 2.3.1.1. that for sulfur to be soluble it must have S& rings. Amorphous or polymeric sulfur are not soluble. Diffusion of sulfur into synthetic polyisoprene particle requires sulfur to be soluble. The same chapter indicates that with ZDBC, you need only small amount of sulfur since ZDBC is an ultrafast accelerator. The web article at http://www.chemistrymag.org/cji/2007/097032pe.htm entitled 'Effect of adding pyridine ligand on the structure and properties of complex $Zn(S_2CNBz_2)_2$,' by Zhong et al. indicates that zinc dibenzyldithiocarbamate and zinc dipyridinedithiocarbamate also have similar functionality of catalytic activity with sulfur. The wetting agent facilitates wetting of the polyisoprene particles and brings soluble sulfur with ring structure broken by zinc dithiocarbomate catalytic action into contact with the surface of the polyisoprene particles and permeation of sulfur occurs during processing time provided. The pre-vulcanized structure of the aqueous latex emulsion is stable for a prolonged period of time, e.g., as long as two months at the aqueous latex emulsion holding temperature without the problems of flocking and latex emulsion instability unlike the "precuring" procedure of U.S. Pat. No. 6,828,387 to Wang, which provides latex emulsion stable only for a maximum period of 8 days and is thus unsuited for manufacturing condoms.

Sulfur is preferably present in the synthetic polyisoprene latex emulsion in an amount of about 0.8-1.8 wt %, based on the dry weight of polyisoprene. If zinc oxide is used, preferably it is present in an amount of about 0-0.5 wt %, based on the dry weight of polyisoprene, whereas, zinc diethyldithiocarbamate or zinc dibutyldithiocarbamate is used it is preferably present in an amount of about 0.3-1.0 wt % or more preferably about 0.3-0.45 wt %, based on the dry weight of polyisoprene.

Examples of suitable wetting agents include, but are not limited to, salts (e.g., sodium salt or potassium salt) of fatty acids, which are anionic, e.g., sodium stearate, sodium oleate, and potassium caprylate. Potassium caprylate is advantageously used with a salt of a short-chain fatty acid, SDBS and polyoxyethylene cetyl/stearyl ether. Potassium caprylate is used in an amount of 0.1-0.5 wt %, based on the dry weight of polyisoprene.

The penetration of the components of the pre-vulcanizing composition into the polyisoprene particles is a strong function of the polyisoprene particle size and size distribution. Typically, smaller particles have a larger surface area, and the components of the pre-vulcanizing composition penetrate these small particles more rapidly. However, these larger surface areas result in more inter-particle regions over intra-particle regions since those smaller particles tends to pre-vulcanize faster than larger particles which are not only larger particles but they are aggregates of smaller particles and are more difficult to pre-vulcanize. In contrast, larger particles have a smaller surface area, and the components of the pre-vulcanizing composition penetrate these large particles more slowly. The smaller surface areas result in less inter-particle regions. Therefore, there is a delicate balance in selecting the size and size range distribution of the polyisoprene particles to produce optimal strength properties that balance pre-vulcanization intra-particle cross-linking with post-vulcanization inter-particle cross-linking. As indicated above, particles in the range of about 0.2-2 micrometers provide optimal results. The penetration of the components of the pre-vulcanizing composition into the polyisoprene particles is also a function of the diffusion process, itself, which is a linear function of time and an exponential function of temperature, reflecting a thermally activated process. Therefore, increasing the temperature by a few degrees during the pre-vulcanization step increases significantly the pre-vulcanization rate. For example, pre-vulcanization at room temperature requires about 12 hours of maturation after the mixing process. However faster pre-curing is typically avoided so as to prevent pre-vulcanization taking place only on periphery of large aggregates as that would result in poor ultimate strength properties of the film: this is the case hardening reaction and the use of potassium caprylate has demonstrated that it would facilitate transporting curative agents into the particles thus accelerating the rate of pre-vulcanization.

The method comprises adding a latex-stabilizing composition, such as one comprising a surfactant package of at least one surfactant, such as 15% Hostapur anionic surfactant. The surfactant is present in an amount of about 0.1-0.5 wt %, based on the dry weight of the synthetic polyisoprene. Upon addition of the latex-stabilizing composition, the emulsion is stirred, e.g., for about 12 hours, to keep the synthetic polyisoprene particles from touching each other.

The method further comprises the steps of adding post-vulcanization composition to the synthetic polyisoprene latex emulsion with accelerators selected from the group consisting of reactive zinc oxide, zinc based accelerators: ZDEC, ZBEC and ZDBC. If reactive zinc oxide is present, preferably it is present in an amount of about 0 to 0.5 wt %, based on the dry weight of synthetic polyisoprene. The composition thus produced is stable for up to about 60 days at 25° C. and can be used in a production line.

This method may also produce synthetic polyisoprene probe covers. Since the probe cover is devoid of any nitrosamine the cancer causing agents are not transferred to the user thereby minimizing cancer risk.

Table I below shows an example of a composition that exhibits pre-vulcanization behavior. A typical mixing sequence of the aqueous synthetic latex emulsion is illustrated. The table lists the steps and the time period involved.

TABLE 1

| Formulation | Kg |
| --- | --- |
| Synthetic Latex agitate 15 min | 600 |
| Colloidal Sulfur agitate 15 min | 7.8 |
| 15% Hostapur SAS | 6.48 |
| 10% Potassium Oleate | 3.78 |
| 15% Eumulgin | 7.68 |
| Disperacc HRZ50 agitate 15 min | 0.36 |
| Dispernox L50 agitate 15 min | 3.89 |
| Disperacc ZDEC agitate 15 min | 3.89 |
| Disperacc ZBEC agitate 15 min | 0.79 |
| 15% Hostapur SAS | 1.20 |
| Disperacc ZDBC agitate 15 min | 0.72 |
| 1.23% Potassium Hydroxide | 0.38 KOH 28.8 $H_2O$ |
| Agitate | 12 hr |

Thus, the present invention further provides a method of forming a synthetic polyisoprene latex condom article. The former can be any suitable former as is known in the art. The method comprises dipping a condom former in the above-described pre-vulcanized synthetic polyisoprene aqueous latex emulsion composition with a solid content of 40 to 60% with a viscosity of 20 to 30 seconds, to form a thin layer of latex film with a thickness of 25 to 35 microns with individual particles of pre-vulcanized synthetic polyisoprene touching each other on the surface of the former. The swelling index in toluene is 100 to 130% after 20 minutes exposure of a cast disk of synthetic polyisoprene.

After the first layer of latex film is not runny with a typical thickness of 25 to 35 microns, the condom former is dipped a second time into a prevulcanized synthetic polyisoprene emulsion to form into a combined thicker latex layer of about 45 to 80 microns. This enhanced thickness of the latex layer prevents tearing as the condom donned.

The tensile properties of condoms produced are shown below in Table II.

TABLE II

| Sample No. | Extension at break (mm) | | Breaking Load (N) | | Elongation (%) | | Tensile Strength (Mpa) | |
|---|---|---|---|---|---|---|---|---|
| | Naked | Foil | Naked | Foil | Naked | Foil | Naked | Foil |
| 1 | 499.3 | 468.5 | 65.0 | 61.0 | 972.69 | 913.46 | 21.96 | 20.61 |
| 2 | 496.7 | 472.0 | 68.0 | 67.0 | 967.69 | 920.19 | 23.29 | 23.59 |
| 3 | 498.0 | 455.9 | 72.0 | 59.0 | 950.00 | 870.57 | 24.66 | 20.49 |
| 4 | 470.2 | 469.0 | 69.0 | 69.0 | 916.73 | 914.42 | 23.96 | 23.96 |
| 5 | 499.8 | 442.0 | 70.0 | 54.0 | 963.43 | 853.33 | 24.31 | 19.01 |
| 6 | 483.5 | 489.0 | 72.0 | 71.0 | 932.38 | 942.86 | 24.66 | 25.00 |
| 7 | 492.5 | 501.0 | 71.0 | 75.0 | 959.62 | 975.96 | 24.65 | 25.68 |
| 8 | 489.7 | 472.0 | 72.0 | 63.0 | 934.34 | 900.94 | 25.00 | 21.88 |
| 9 | 469.5 | 472.0 | 69.0 | 67.0 | 905.71 | 910.48 | 23.63 | 24.28 |
| 10 | 500.0 | 495.1 | 67.0 | 64.0 | 963.81 | 954.48 | 22.95 | 22.86 |
| 11 | 505.0 | 469.0 | 79.0 | 61.0 | 973.33 | 904.76 | 27.05 | 21.18 |
| 12 | 462.5 | 467.0 | 62.0 | 63.5 | 901.92 | 910.58 | 21.23 | 22.36 |
| 13 | 453.5 | 469.0 | 57.0 | 65.5 | 875.24 | 904.76 | 19.26 | 23.06 |

The nitrosamine content was measured in several samples as shown below in Table III A &B.

TABLE IIIA

| | N-Nitrosamines | | |
|---|---|---|---|
| | Batch No. I-GNWLA06P-180238 B.5 Sample No. I04/2018 | Batch No. I-GNWLA06P-180239 B.5 Sample No. H04/2018 | Batch No. I-GNWLA06P-180240 B.5 Sample No. J04/2018 |
| | Descriptions | | |
| | Colour Natural | Colour Natural | Colour Natural |
| N-nitrosodimethylamine (NDMA) | Not Detected[a] | Not Detected[a] | Not Detected[a] |
| N-nitrosodiethylamine (NDEA) | Not Detected[a] | Not Detected[a] | Not Detected[a] |
| N-nitrosodipropylamine (NDPA) | Not Detected[a] | Not Detected[a] | Not Detected[a] |
| N-nitrosodibutylamine (NDBA) | Not Detected[a] | Not Detected[a] | Not Detected[a] |
| N-nitrosopiperidine (NPIP) | Not Detected[a] | Not Detected[a] | Not Detected[a] |
| N-nitrosopyrrolidine (NPYR) | Not Detected[a] | Not Detected[a] | Not Detected[a] |
| N-nitrosomorpholine (NMOR) | Not Detected[a] | Not Detected[a] | Not Detected[a] |
| N-nitrosodibenzylamine (NDBzA) | Not Detected[a] | Not Detected[a] | Not Detected[a] |
| N-nitroso-N-methyl-N-phenylamine (NMPhA) | Not Detected[a] | Not Detected[a] | Not Detected[a] |
| N-nitroso-N-ethyl-N-phenylamine (NEPhA) | Not Detected[a] | Not Detected[a] | Not Detected[a] |
| N-nitrosodiisononylamine (NDiNA) | Not Detected[a] | Not Detected[a] | Not Detected[a] |

[a]The method detection limit was 10 ng/g, where 1 ng/g = 1 ppb

TABLE III B

The test result of N-Nitrosamine - 2016
Site: LCB
Lab: TUV SUD Singapore
Date of Analysis: 8 Mar. 2016-15 Mar. 2016

| | N-Nitrosamines Testing Parameters | |
|---|---|---|
| | Batch No. G-GNWMA03-160201 B.6 Sample No. G01/2016 | Batch No. G-GNWLA01-160203 B.10 Sample No. H01/2016 |
| | Descriptions | |
| | Colour Natural Leach tank 1 days, 2 Dip tank, 65° C. | Colour Natural Leach tank 3 days, 2 Dip tank, 55° C. |
| N-nitrosodimethylamine (NDMA) | Not Detected | Not Detected |
| N-nitrosodiethylamine (NDEA) | Not Detected | Not Detected |
| N-nitrosodipropylamine (NDPA) | Not Detected | Not Detected |
| N-nitrosodibutylamine (NDBA) | Not Detected | Not Detected |
| N-nitrosopiperidine (NPIP) | Not Detected | Not Detected |
| N-nitrosopyrrolidine (NPYR) | Not Detected | Not Detected |
| N-nitrosomorpholine (NMOR) | Not Detected | Not Detected |
| N-nitrosodibenzylamine (NDBzA) | Not Detected | Not Detected |
| N-nitroso-N-methyl-N-phenylamine (NMPhA) | Not Detected | Not Detected |
| N-nitroso-N-ethyl-N-phenylamine (NEPhA) | Not Detected | Not Detected |
| N-nitrosodiisononylamine (NDiNA) | Not Detected | Not Detected | a) The method detection limit was 10 ng/g, where 1 ng/g = 1 ppb
Remark: Production Period February 2016

FIG. 1 shows the steps involved in creating synthetic polyisoprene latex that is free from nitrosamines. It illustrates the process flow chart for the manufacture of dipped and cured synthetic polyisoprene condom. The process begins stripping previously made condom formers. The former is dipped in a nitric acid bath, followed by a dip in two acid baths. The former is then dried in an oven. It is then dipped in pre-vulcanized synthetic latex #1 which has about 50 to 55% total solid content at 20 to 30° C. The viscosity of the latex is about 18 to 22 sec using Ford cup #4. The thickness of latex layer formed is about 25-35 microns. The latex layer coated former is dried to ensure the latex is no longer runny. Next, the latex coated condom former is dipped in a second pre-vulcanized synthetic latex solution, which has a solid content of 50 to 55% but with a viscosity of 25-30 sec ford cup #6. The second latex dip produces a thicker layer of synthetic latex layer typically making the total thickness 45 to 80 microns. The thicker layer prevents tearing of condoms.

All references, including publications, patent applications, and patents, cited herein are hereby incorporated by reference to the same extent as if each reference were individually and specifically indicated to be incorporated by reference and were set forth in its entirety herein.

The use of the terms "a," "an," "the," and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to illuminate better the invention and does not pose a limitation on the scope of the invention, unless otherwise claimed. No language in the specification should be construed as indicating any non-claimed element as essential to the practice of the invention.

What is claimed is:

1. A condom comprising: a. a latex synthesized from a pre-vulcanized latex emulsion, comprising: i. pre-vulcanized synthetic polyisoprene latex having a swelling index from 100% to 130%; ii. accelerators, each containing nitrogen, including: 1. zinc diethyldithiocarbamate; 2. zinc dibenzyldithiocarbamate; 3. zinc dibutyldithiocarbamate; and iii. an anionic surfactant wherein the anionic surfactant is sodium C14-17 alkyl sec sulfonate selected from the group consisting of alkyl sulphonates, alkyl aryl sulphonates, olefin sulphonates, and alcohol sulphates; and iv. water, wherein said condom has strength, is highly stretchable up to and about 900%, and wherein the condom releases less than 10 ppb (parts per billion) of nitrosamine and the condom contains nitrogen.

2. The condom of claim 1, wherein the condom has a width of 49 mm to 60 mm and a length of minimum 160 mm with a thickness of 0.045 mm to 0.090 mm.

3. The condom article of claim 1, wherein the condom has a burst volume greater than 22 liters, and burst pressure of greater than 1 kPa.

4. The condom of claim 1, wherein the latex is cured at a temperature from 90° C. and 120° C. for a period of 5 to 20 minutes.

5. The condom of claim 1, wherein the condom releases less than 1 ppb of nitrosamine.

6. The condom of claim 1, wherein the pre-vulcanized synthetic polyisoprene latex has a swelling index of 130%.

* * * * *